United States Patent
Wu et al.

(10) Patent No.: US 10,175,202 B2
(45) Date of Patent: Jan. 8, 2019

(54) MAGNETOSTRICTIVELY INDUCED GUIDED WAVE SENSOR DEVICE

(71) Applicant: HUAZHONG UNIVERSITY OF SCIENCE AND TECHNOLOGY, Wuhan, Hubei (CN)

(72) Inventors: Xinjun Wu, Hubei (CN); Ming Cong, Hubei (CN); Gongtian Shen, Hubei (CN); Jie Chen, Hubei (CN)

(73) Assignee: HUAZHONG UNIVERSITY OF SCIENCE AND TECHNOLOGY, Wuhan, Hubei (CN)

( * ) Notice: Subject to any disclaimer, the term of this patent is extended or adjusted under 35 U.S.C. 154(b) by 78 days.

(21) Appl. No.: 15/305,988

(22) PCT Filed: Apr. 7, 2016

(86) PCT No.: PCT/CN2016/078676
§ 371 (c)(1),
(2) Date: Oct. 21, 2016

(87) PCT Pub. No.: WO2017/080133
PCT Pub. Date: May 18, 2017

(65) Prior Publication Data
US 2017/0269037 A1     Sep. 21, 2017

(30) Foreign Application Priority Data
Nov. 13, 2015   (CN) .......................... 2015 1 0777045

(51) Int. Cl.
*G01N 27/85*     (2006.01)
*G01N 29/34*     (2006.01)
(Continued)

(52) U.S. Cl.
CPC ........... *G01N 27/85* (2013.01); *G01N 29/041* (2013.01); *G01N 29/223* (2013.01);
(Continued)

(58) Field of Classification Search
CPC combination set(s) only.
See application file for complete search history.

(56) References Cited

U.S. PATENT DOCUMENTS 3,504,277 A * 3/1970 Mogilevsky ....... G01R 33/0283
324/257
5,456,113 A   10/1995 Kwun et al.
(Continued)

FOREIGN PATENT DOCUMENTS

CN         1183142       5/1998
CN       101451976       6/2009
(Continued)

*Primary Examiner* — Jay Patidar
(74) *Attorney, Agent, or Firm* — Hamre, Schumann, Mueller & Larson, P.C.

(57) ABSTRACT

Provided is a test sensor using a magnetostrictively induced guided wave based on an open magnetic circuit, comprising an excitation coil, a receiving coil and a magnetic device, the magnetic device comprises multiple test modules circumferentially and uniformly disposed thereon so as to be absorbed to the outer side of a to-be-tested slender component, each test module comprises a housing, a permanent magnet and a magnetic plate, two adjacent housings are connected to each other via an adjusting device, the excitation coil and the receiving coil are disposed in the vicinity of the test module, and are coaxially fit on the outer side of the to-be-tested slender component, the excitation coil operates to generate induced voltage in the receiving coil after the sinusoidal alternating current is input, and a computer can determine whether a defect occurs in the to-be-tested slender component after receiving the induced voltage. The sensor of the invention features simple structure, small size, light weight and convenient installation. Moreover, by serially connecting the sensor with multi-layered test coils (Continued)

disposed on both sides of the permanent magnet, it is possible to enhance an amplitude of a test signal, and to improve test sensitivity.

6 Claims, 3 Drawing Sheets

(51) Int. Cl.
  *G01N 29/04* (2006.01)
  *G01N 29/22* (2006.01)
  *G01N 29/24* (2006.01)
(52) U.S. Cl.
  CPC ......... *G01N 29/2412* (2013.01); *G01N 29/34* (2013.01); *G01N 2291/0289* (2013.01); *G01N 2291/2634* (2013.01)

(56) References Cited

U.S. PATENT DOCUMENTS

| | | | |
|---|---|---|---|
| 5,581,037 A | 12/1996 | Kwun et al. | |
| 2001/0022514 A1* | 9/2001 | Light | G01N 17/006 324/240 |
| 2010/0052670 A1* | 3/2010 | Kwun | G01N 29/2412 324/240 |
| 2018/0217105 A1* | 8/2018 | Borigo | G01N 29/2412 |

FOREIGN PATENT DOCUMENTS

| | | |
|---|---|---|
| CN | 101545755 | 9/2009 |
| CN | 105445362 | 3/2016 |
| JP | 2001174343 | 6/2001 |

* cited by examiner

MAGNETOSTRICTIVELY INDUCED GUIDED WAVE SENSOR DEVICE

TECHNICAL FIELD

The invention relates to the field of nondestructive testing, and more particularly to a test method and sensor using a magnetostrictively induced guided wave based on an open magnetic circuit.

BACKGROUND OF THE INVENTION

With the fast development of industries like petroleum, chemistry, transportation and so on, pipes and cables are widely used. Failures of pipes, such as erosion, perforation or wall thickness reduction, often take place due to high temperature, high pressure, flushing and so on, and reasons like fatigue, raining and so on may cause cables to be broken or corroded. To prevent accidents, it is required to periodically test and maintain the pipes and the cables. Since the ultrasonic guided wave testing technique can fast test a part of the pipe or the cable by a single-point excitation and no need to move sensors during the testing process, it has been widely used in the relevant field.

The magnetostrictive guided wave testing technique has the advantages of no contact, no polishing process on the surface of the tested component, high testing efficiency, and it is applicable for on-site testing of a slender component. U.S. Pat. No. 5,456,113A discloses a method for the nondestructive evaluation of the ferromagnetic material to detect and locate fractures, cracks, and other anomalies based on the magnetostrictive guided waves, U.S. Pat. No. 5,581,037A also discloses a method for the inspection of ferromagnetic cylindrical shell structures such as pipes and pipes based on the magnetostrictive guided waves. The above two testing methods make use of a conventional closed magnetic circuit to axially magnetize the tested cable or pipe, by the way of circumferentially arranging a certain number of magnetizers on the surface to provide a uniform axial static magnetic field. These two methods are non-contact testing methods, namely there is no need to polish the surface of the position for the sensor installation, which results in a high testing efficiency. However, since each magnetizer has large size and heavy weight, it is required to assemble and disassemble multiple magnetizers during the guided wave testing process, which reduces the testing efficiency to a certain extent. Meanwhile, during on-site testing, the number of the tested slender components is always comparatively large, the testing method of using multiple magnetizers to provide the axial static magnetic field has some disadvantages such as inconvenient installation, as well as time-consuming and laborious operation.

SUMMARY OF THE INVENTION

In view of the above-mentioned problems, it is an objective of the invention to provide a test method and a sensor using a magnetostrictively induced guided wave based on an open magnetic circuit capable of realizing excitation and receiving of a magnetostrictively induced longitudinal ultrasonic guided wave, as well as test by interaction between an axial static magnetic field generated at the edge of a permanent magnet and an axial alternating magnetic field of a solenoid coil.

In order to achieve the above goals, in accordance with an embodiment of the invention, provided is a test sensor using a magnetostrictively induced guided wave based on an open magnetic circuit, comprising an excitation coil, a receiving coil and a magnetic device, the magnetic device comprises multiple test modules circumferentially and uniformly disposed thereon so as to be absorbed to the outer side of a to-be-tested slender component, each test module comprises a housing, a permanent magnet and a magnetic plate, the permanent magnet is fixedly disposed in the housing, a polarization direction thereof is vertical to an axis of the to-be-tested slender component, and the magnetic plate is fixedly disposed on the housing and contactable with the to-be-tested slender component, an end of each permanent magnet in the vicinity of the slender component is of the same polarity, two adjacent housings are connected to each other via an adjusting device, the adjusting device comprises an adjusting slider and a pair of adjusting screws, a strip-shaped hole is disposed on the adjusting slider, and the adjusting screws passes through the adjusting slider via the strip-shaped hole, and are fixedly connected to the housing, the excitation coil and the receiving coil are coaxially fit on the outer side of the to-be-tested slender component, the excitation coil operates to generate an alternating magnetic field along an axis of the to-be-tested slender component on the surface thereof after sinusoidal alternating current is input, the alternating magnetic field interacts with a static magnetic field generated by the permanent magnet along an axis of the slender component, and further excites a longitudinal ultrasonic guided wave to generate induced voltage in the receiving coil, and a computer can determine whether a defect occurs in the to-be-tested slender component after receiving the induced voltage.

Advantageously, the housing comprises a body and an end cover, the body and the end cover are made from non-magnetic materials, and the end cover is disposed on the body, and operates to enclose the permanent magnet along with the body.

Advantageously, the magnetic plate is made of industrial pure iron or low carbon steel.

Advantageously, the excitation coil and/or the receiving coil is made by winding multiple layers of wires.

Advantageously, the excitation coil and the receiving coil are respectively disposed in the vicinity of both sides of the housing.

In accordance with another embodiment of the invention, provided is a test device, comprising the above-mentioned test sensor, a signal generator, a power amplifier, a signal pre-processor, an A/D converter and a computer, the power amplifier is electrically connected to an excitation coil, the signal pre-processor is electrically connected to a receiving coil, the computer controls the signal generator to generate a sinusoidal pulse current signal, then the sinusoidal pulse current signal is input to the test sensor after being amplified by the power amplifier, and excites a longitudinal ultrasonic guided wave in a to-be-tested slender component, meanwhile, an electric signal generated by the longitudinal ultrasonic guided wave in the receiving coil is processed by the signal pre-processor and the A/D converter, and then input to the computer thereby generating an ultrasonic guided wave test signal operating to detect whether a defect occurs in the to-be-tested slender component.

In accordance with a further embodiment of the invention, provided is a test method using a magnetostrictively induced guided wave based on an open magnetic circuit, the method operating to excite and receive a longitudinal ultrasonic guided wave on a to-be-tested slender component and to detect a defect occurred in the slender component, and comprising steps of:

1) circumferentially disposing multiple permanent magnets on the outer side of the slender component, a polarization direction of each permanent magnet being vertical to an axis of the slender component, so as to magnetize the slender component, and to generate an axial static magnetic field on the surface of the slender component degrading gradually, an end of each permanent magnet in the vicinity of the slender component being of the same polarity;

2) axially winding an excitation coil and a receiving coil on the slender component, a winding direction of the excitation coil being opposite to that of the receiving coil;

3) inputting a sinusoidal alternating current to the excitation coil via a signal generator and a power amplifier by a computer, so as to generate an alternating magnetic field along an axis of the slender component on the surface thereof, and interacting with the axial static magnetic field generated by the permanent magnet by the alternating magnetic field, so as to excites a longitudinal ultrasonic guided wave in the slender component to generate an induced voltage in the receiving coil; and 4) receiving the induced voltage via a signal processor and an A/D converter, and determining whether a defect occurs in the slender component according to the induced voltage by the computer.

In accordance with a still another embodiment of the invention, provided is a test method using a magnetostrictively induced guided wave based on an open magnetic circuit, the method operating to excite and receive a longitudinal ultrasonic guided wave on a to-be-tested slender component and to detect a defect occurred in the slender component, and comprising steps of:

1) circumferentially disposing multiple permanent magnets on the outer side of the slender component, a polarization direction of each permanent magnet being vertical to an axis of the slender component, so as to magnetize the slender component, and to generate an axial static magnetic field on the surface of the slender component degrading gradually, an end of each permanent magnet in the vicinity of the slender component being of the same polarity;

2) axially winding a pair of first solenoid coils on the slender component, the first solenoid coils being connected to each other via a first wire thereby forming an excitation coil, and a pair of second solenoid coils on the slender component, the second solenoid coils being connected to each other via a second wire thereby forming a receiving coil, and respectively fit on a corresponding first solenoid coil, winding direction of the first solenoid coils being opposite, and winding direction of the second solenoid coils being opposite;

3) inputting a sinusoidal alternating current to the excitation coil via a signal generator and a power amplifier by a computer, so as to generate an alternating magnetic field along an axis of the slender component on the surface thereof, and interacting with the axial static magnetic field generated by the permanent magnet by the alternating magnetic field, so as to excites a longitudinal ultrasonic guided wave in the slender component to generate an induced voltage in the receiving coil; and 4) receiving the induced voltage via a signal processor and an A/D converter, and determining whether a defect occurs in the slender component according to the induced voltage by the computer.

In accordance with a still further embodiment of the invention, provided is a test method using a magnetostrictively induced guided wave based on an open magnetic circuit, the method operating to excite and receive a longitudinal ultrasonic guided wave on a to-be-tested slender component and to detect a defect occurred in the slender component, and comprising steps of:

1) axially disposing a pair of test devices on the slender component, each test device comprising multiple permanent magnets circumferentially disposed on the outer side of the slender component, a polarization direction of each permanent magnet being vertical to an axis of the slender component, so as to magnetize the slender component, and to generate an axial static magnetic field on the surface of the slender component degrading gradually, an end of each permanent magnet in the vicinity of the slender component being of the same polarity;

2) axially winding a pair of first solenoid coils on the slender component, the first solenoid coils being connected to each other via a first wire thereby forming an excitation coil, and a pair of second solenoid coils on the slender component, the second solenoid coils being connected to each other via a second wire thereby forming a receiving coil, and respectively fit on a corresponding first solenoid coil, winding direction of the first solenoid coils being opposite, and winding direction of the second solenoid coils being opposite;

3) inputting a sinusoidal alternating current to the excitation coil via a signal generator and a power amplifier by a computer, so as to generate an alternating magnetic field along an axis of the slender component on the surface thereof, and interacting with the axial static magnetic field generated by the permanent magnet by the alternating magnetic field, so as to excites a longitudinal ultrasonic guided wave in the slender component to generate an induced voltage in the receiving coil; and 4) receiving the induced voltage via a signal processor and an A/D converter, and determining whether a defect occurs in the slender component according to the induced voltage by the computer.

Advantageously, the first solenoid coil and/or the second solenoid coil is made by winding multiple layers of wires.

To summarize, the invention has the following advantages over the prior art:

Being different from a conventional sensor based on a closed magnetic circuit in which a uniform and axial static magnetic field is provided by a magnetizer, the test sensor using a magnetostrictively induced guided wave based on an open magnetic circuit of the invention provides an axial static magnetic field by using a single-row and circumferentially arranged magnet array, which features an open magnetic circuit. In addition, the sensor of the invention features small size, light weight and convenient installation. Moreover, the sensor is capable of enhancing the amplitude of the test signal and increasing test accuracy by serial connection of multi-layered test coils on both sides of the permanent magnet.

BRIEF DESCRIPTION OF ACCOMPANYING DRAWINGS

In all figures, identical labels are used for representing identical elements or structure, in which: 1—adjusting slider; 2—adjusting screw; 3—body; 4—end cover; 5—permanent magnet; 6—magnetic plate; 7—excitation coil; 8—receiving coil; 9—to-be-tested slender component; 10—computer; 11—signal generator; 12—power amplifier; 13—signal pre-processor; 14—A/D converter.

SPECIFIC EMBODIMENTS OF THE INVENTION

For clear understanding of the objectives, features and advantages of the invention, detailed description of the invention will be given below in conjunction with accompanying drawings and specific embodiments. It should be noted that the embodiments are only meant to explain the invention, and not to limit the scope of the invention.

Figure 1:
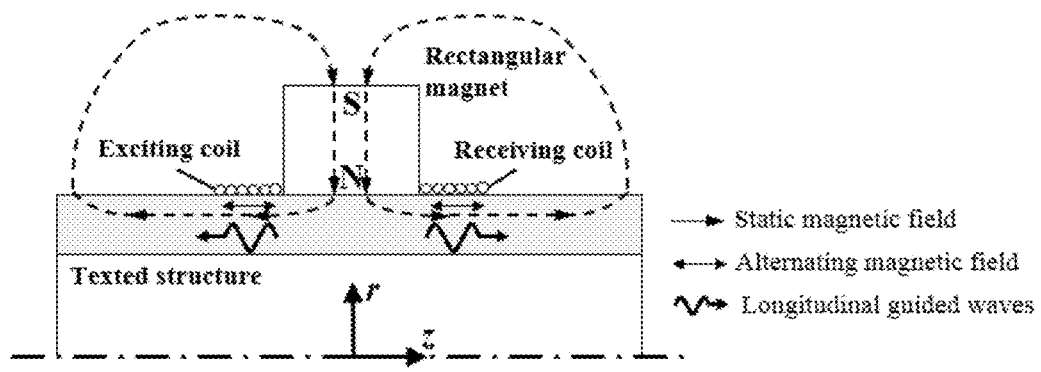
FIG. 1 illustrates test principle of a test sensor using a magnetostrictively induced guided wave based on an open magnetic circuit of an exemplary embodiment of the invention.
Figure 2:
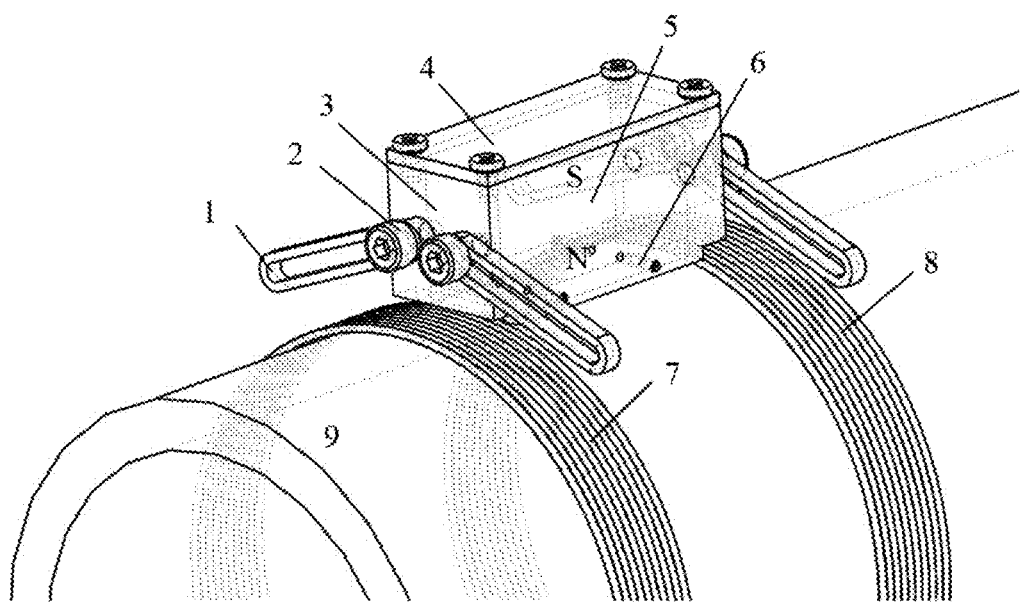
FIG. 2 is a schematic view of a test sensor using a magnetostrictively induced guided wave based on an open magnetic circuit of an exemplary embodiment of the invention.
Figure 3:
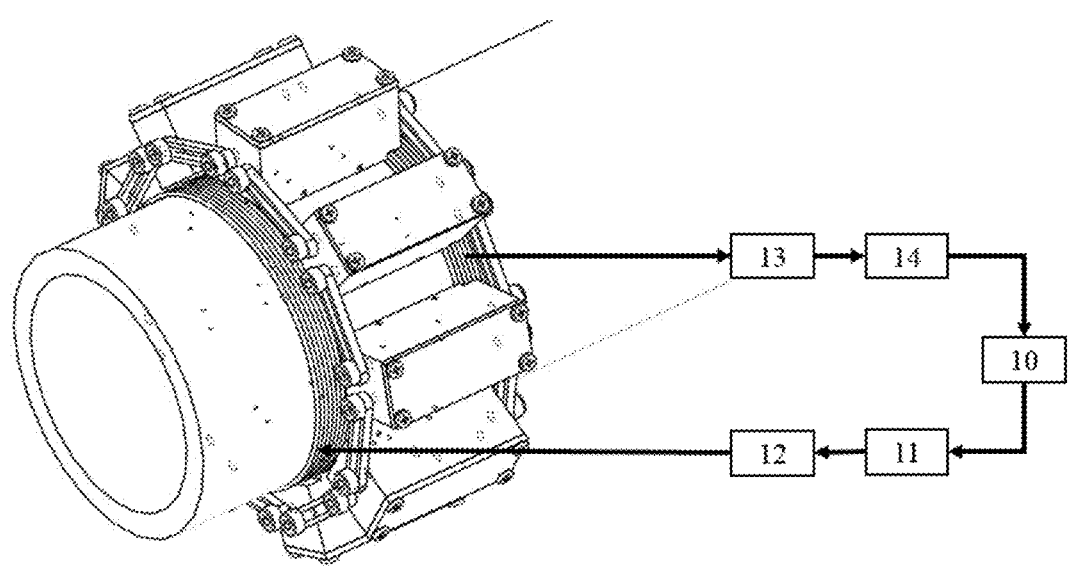
FIG. 3 is a schematic view of a test device comprising a test sensor using a magnetostrictively induced guided wave based on an open magnetic circuit of an exemplary embodiment of the invention.

As shown in FIGS. 1 to 3, a test sensor using a magnetostrictively induced guided wave based on an open magnetic circuit of the invention comprises an excitation coil 7, a receiving coil 8 and a magnetic device.

The magnetic device comprises multiple test modules circumferentially and uniformly disposed thereon so as to be absorbed to the outer side of a to-be-tested slender component 9.

Each test module comprises a housing, a permanent magnet 5 and a magnetic plate 6, the permanent magnet 5 is fixedly disposed in the housing, a polarization direction thereof is vertical to an axis of the to-be-tested slender component 9, and the magnetic plate 6 is fixedly disposed on the housing and contactable with the to-be-tested slender component 9. Advantageously, the housing comprises a body 3 and an end cover 4, the body 3 and the end cover 4 are made from non-magnetic materials, and the end cover 4 is disposed on the body 3, and operates to enclose the permanent magnet along with the body 3. The magnetic plate 6 is made of industrial pure iron or low carbon steel.

An end of each permanent magnet in the vicinity of the slender component 9 is of the same polarity.

Two adjacent housings are connected to each other via an adjusting device, the adjusting device comprises an adjusting slider 1 and a pair of adjusting screws 2, a strip-shaped hole is disposed on the adjusting slider 1, and the adjusting screws 2 passes through the adjusting slider 1 via the strip-shaped hole, and are fixedly connected to the housing.

The excitation coil 7 and the receiving coil 8 are coaxially fit on the outer side of the to-be-tested slender component 9, the excitation coil 7 operates to generate an alternating magnetic field along an axis of the to-be-tested slender component 9 on the surface thereof after sinusoidal alternating current is input, the alternating magnetic field interacts with a static magnetic field generated by the permanent magnet 5 along an axis of the slender component 9, and further excites a longitudinal ultrasonic guided wave to generate induced voltage in the receiving coil 8, and a computer 10 can determine whether a defect occurs in the to-be-tested slender component 9 after receiving the induced voltage. Advantageously, the excitation coil 7 and/or the receiving coil 8 is made by winding multiple layers of wires. The excitation coil 7 and the receiving coil 8 are respectively disposed in the vicinity of both ends of the housing, making it possible to enhance an amplitude of a test signal by exciting and receiving the ultrasonic guided wave using a peak point of an axial magnetic field at the edge of the permanent magnet 5.

After being powered with alternating current, the excitation coil 7 generates the alternating magnetic field along the axis of the to-be-tested slender component. The alternating magnetic field interacts with an axial static magnetic field generated by a rectangular magnet, thus generating magnetostrictive strain, and further the ultrasonic guided wave in the to-be-tested slender component for nondestructive testing. Meanwhile, the ultrasonic guided wave carrying the slender component's information causes variation in magnetic induction intensity thereof, and generates an electric signal carrying test information in the receiving coil 8, it is possible to obtain test results according to the electric signal.

Referring to FIG. 2, the test modules are circumferentially arranged, and the body 3 and the end cover 4 are preferably made of nylon materials. The magnetic plate 6 is disposed on the rectangular magnet, and fixed on the body 3 via a screw. A polarization direction of the rectangular magnet is vertical to an axis of the to-be-tested slender component 9. The excitation coil 7 and the receiving coil 8 respectively tightly abuts against both sides of the magnetic plate 6, and are wound on the surface of the to-be-tested slender component. Both coils can enhance an amplitude of the test signal and thus improving test sensitivity by using serial connection or multiple layers of coils. Winding directions of coils on both sides of the rectangular magnet are opposite, and those of coils on the same side thereof are the same. The adjusting screw 2 passes through the adjusting slider 1 and is connected to the body 3.

Referring to FIG. 3, multiple test modules that are circumferentially arranged form the test sensor of the invention, and the adjusting slider 1 operates to connect each test module. By changing a relation of the adjusting screw 2 with respect to the adjusting slider 1, it is possible to control a distance between adjacent test modules so as to adapt to test conditions of pipes or cables with different diameters. Both sides of a test module along an axis of the to-be-tested pipe are connected to those of another test module adjacent thereto via the adjusting slider 1, so as to ensure axial installation positions of different test modules are the same. Meanwhile, it is possible to determine the number of the test modules meeting test requirement according to the diameter of the pipe, which makes the invention feature good reconfiguration, small sensor size, light weight, and convenient installation.

The computer 10 controls a signal generator 11 to generate a sinusoidal pulse current signal, which is input to the test sensor after being amplified by a power amplifier 12, and the excitation coil 7 excites an ultrasonic guided wave in the to-be-tested pipe based on magnetostrictive effect. Meanwhile, the signal pre-processor 13 and the A/D converter 14 processes an electric signal generated by the ultrasonic guided wave in the receiving coil 8, and then the electric signal is input to the computer 10 thereby generating an ultrasonic guided wave test signal, and the test process is completed.

Two test methods named 'self-excitation and self-receiving' will be described hereinafter.

A first test method using a magnetostrictively induced guided wave based on an open magnetic circuit operates to excite and receive a longitudinal ultrasonic guided wave on a to-be-tested slender component and to detect a defect occurred in the slender component, and comprises steps of:

1) circumferentially disposing multiple permanent magnets 5 on the outer side of the slender component, a polarization direction of each permanent magnet 5 being vertical to an axis of the slender component, so as to magnetize the slender component, and to generate an axial static magnetic field on the surface of the slender component degrading gradually, an end of each permanent magnet in the vicinity of the slender component being of the same polarity;

2) axially winding an excitation coil 7 and a receiving coil 8 on the slender component, a winding direction of the excitation coil 7 being opposite to that of the receiving coil 8;

3) inputting a sinusoidal alternating current to the excitation coil 7 via a signal generator 11 and a power amplifier 12 by a computer 10, so as to generate an alternating magnetic field along an axis of the slender component 9 on the surface thereof, and interacting with the axial static magnetic field generated by the permanent magnet 5 by the alternating magnetic field, so as to excite a longitudinal ultrasonic guided wave in the slender component to generate an induced voltage in the receiving coil 8; and 4) receiving the induced voltage via a signal processor and an A/D converter 14, and determining whether a defect occurs in the slender component according to the induced voltage by the computer 10.

A second test method using a magnetostrictively induced guided wave based on an open magnetic circuit operates to excite and receive a longitudinal ultrasonic guided wave on a to-be-tested slender component and to detect a defect occurred in the slender component, and comprises steps of:

1) circumferentially disposing multiple permanent magnets 5 on the outer side of the slender component, a polarization direction of each permanent magnet 5 being vertical to an axis of the slender component, so as to magnetize the slender component, and to generate an axial static magnetic field on the surface of the slender component degrading gradually, an end of each permanent magnet in the vicinity of the slender component being of the same polarity;

2) axially winding a pair of first solenoid coils on the slender component, the first solenoid coils being connected to each other via a first wire thereby forming an excitation coil 7, and a pair of second solenoid coils on the slender component, the second solenoid coils being connected to each other via a second wire thereby forming a receiving coil 8, and respectively fit on a corresponding first solenoid coil, winding direction of the first solenoid coils being opposite, and winding direction of the second solenoid coils being opposite;

3) inputting a sinusoidal alternating current to the excitation coil 7 via a signal generator 11 and a power amplifier 12 by a computer 10, so as to generate an alternating magnetic field along an axis of the slender component 9 on the surface thereof, and interacting with the axial static magnetic field generated by the permanent magnet 5 by the alternating magnetic field, so as to excite a longitudinal ultrasonic guided wave in the slender component to generate an induced voltage in the receiving coil 8; and 4) receiving the induced voltage via a signal processor and an A/D converter 14, and determining whether a defect occurs in the slender component according to the induced voltage by the computer 10.

'self-excitation and self-receiving' means the permanent magnet 5, the excitation coil 7 and the receiving coil 8 disposed on the slender component form a sensor, and the sensor itself can generate an excitation signal and obtain a sensing signal.

Figure 4:
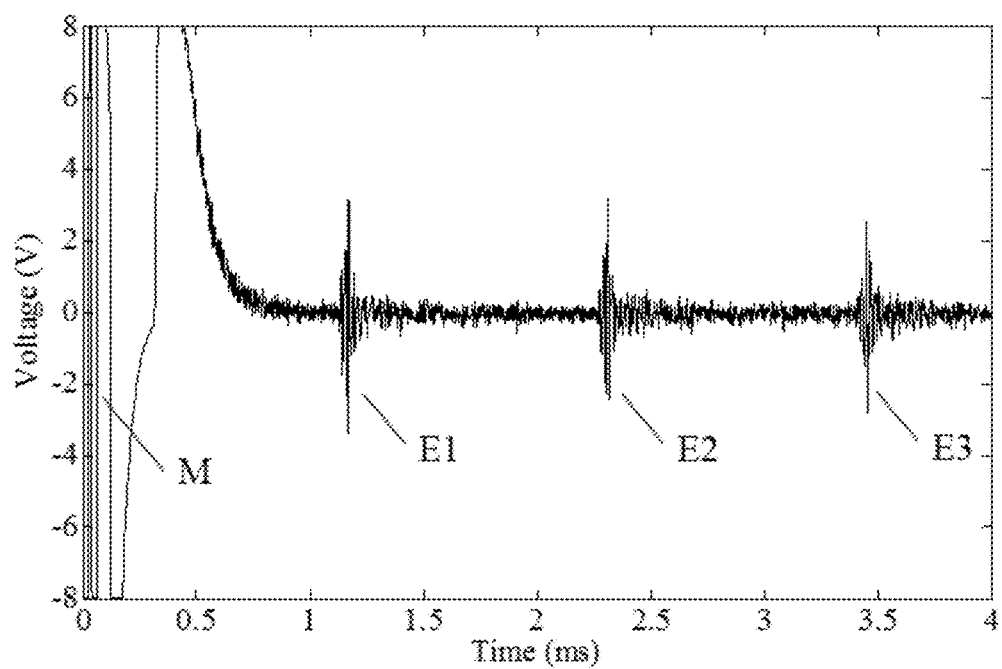
FIG. 4 illustrates a waveform of a test signal obtained on a marking tube by using a so-called 'self-excitation and self-receiving' test method.

FIG. 4 illustrates a waveform of a test signal obtained on a marking tube by using a so-called 'self-excitation and self-receiving' test method, as well as a test sensor of the invention. The marking tube is a carbon steel tube with an outer diameter of 90 mm, a thickness of 8 mm, and a length of 2.8 m. The test sensor is disposed on a left end of the marking tube, nine test modules are circumferentially arranged thereon, connection of coils is shown in FIG. 3, the excitation coil 7 and the receiving coil 8 disposed on both sides of the rectangular magnet are single-layered coil, and an excitation frequency of 50 kHz is used. In FIG. 4, M represents an electromagnetic pulse signal generated by coupling of the excitation coil 7 and the receiving coil 8, E1, E2 and E3 respectively represents a first echo signal, a second echo signal and a third echo signal generated by the ultrasonic guided signal reflected by a right end of the marking tube. It can be seen that an amplitude of the test signal is obvious, and a signal-to-noise ratio is good enough, which indicate the test method using the magnetostrictively induced guided wave is feasible, and features comparatively good test effect.

Next a test method named 'one excitation and one receiving' will be described.

A test method using a magnetostrictively induced guided wave based on an open magnetic circuit operates to excite and receive a longitudinal ultrasonic guided wave on a to-be-tested slender component and to detect a defect occurred in the slender component, and comprises steps of:

1) axially disposing a pair of test devices on the slender component, each test device comprising multiple permanent magnets 5 circumferentially disposed on the outer side of the slender component 9, a polarization direction of each permanent magnet 5 being vertical to an axis of the slender component, so as to magnetize the slender component, and to generate an axial static magnetic field on the surface of the slender component degrading gradually, an end of each permanent magnet in the vicinity of the slender component being of the same polarity;

2) axially winding a pair of first solenoid coils on the slender component, the first solenoid coils being connected to each other via a first wire thereby forming an excitation coil 7, and a pair of second solenoid coils on the slender component, the second solenoid coils being connected to each other via a second wire thereby forming a receiving coil 8, and respectively fit on a corresponding first solenoid coil, winding direction of the first solenoid coils being opposite, and winding direction of the second solenoid coils being opposite; advantageously, each of the first solenoid coil and/or the second solenoid coil is made by winding multiple layers of wires.

3) inputting a sinusoidal alternating current to the excitation coil via a signal generator 11 and a power amplifier 12 by a computer 10, so as to generate an alternating magnetic field along an axis of the slender component 9 on the surface thereof, and interacting with the axial static magnetic field generated by the permanent magnet 5 by the alternating magnetic field, so as to excites a longitudinal ultrasonic guided wave in the slender component to generate an induced voltage in the receiving coil 8; and 4) receiving the induced voltage via a signal processor and an A/D converter 14, and determining whether a defect occurs in the slender component according to the induced voltage by the computer 10.

'one excitation and one receiving' means a permanent magnet 5 and a solenoid coil disposed on one position of the slender component form an excitation sensor, and a permanent magnet 5 and a solenoid coil disposed on the other position of the slender component 5 form a receiving sensor.

Figure 5:
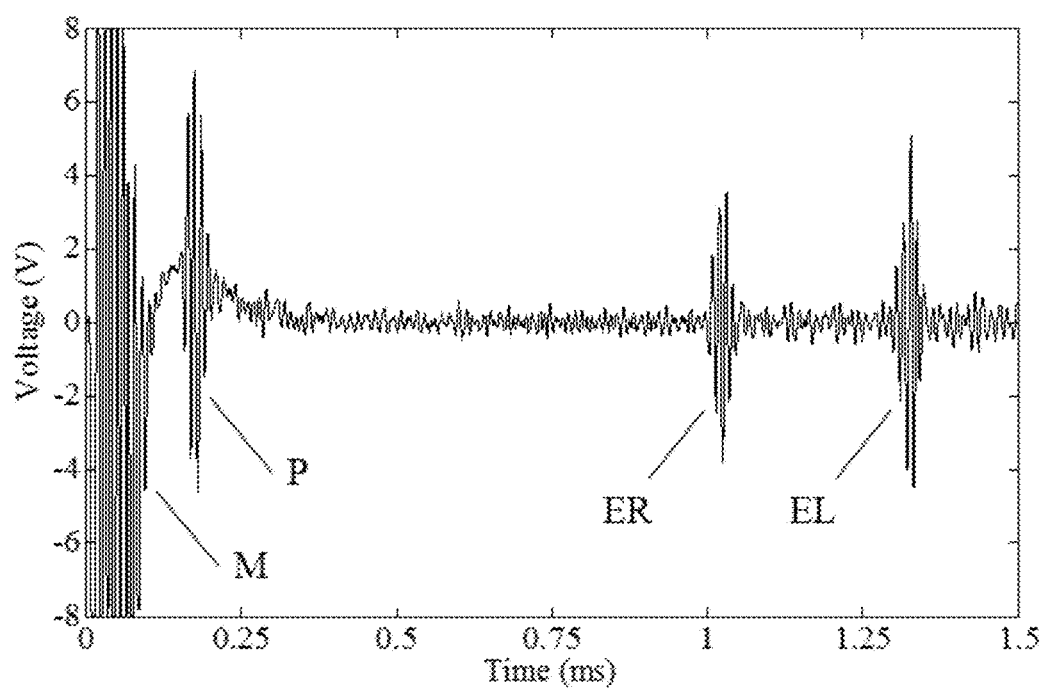
FIG. 5 illustrates a waveform of a test signal obtained on a marking tube by using a so-called 'one excitation and one receiving' test method.

FIG. 5 illustrates a waveform of a test signal obtained on a marking tube by using a so-called 'one excitation and one receiving' test method, as well as a test sensor of the invention. A test method of the excitation coil 7 is the same as that in FIG. 4, an excitation sensor is disposed on a left end of the marking tube, a receiving sensor is disposed at a position 0.8 m away from the excitation sensor, a double-layer coil is used, and coils on both sides of the rectangular magnet are serially connected to form the receiving coil 8, so as to enhance an amplitude of a test signal. An excitation frequency is increased to 120 kHz. In FIG. 5, M represents an electromagnetic pulse signal generated by direct coupling of the excitation coil 7 and the receiving coil 8, P represents a through signal passing the receiving sensor, ER represents an echo signal generated by the ultrasonic guided wave reflected from a right end of the marking tube, EL represents an echo signal generated by the ultrasonic guided wave reflected from a right end and a left end of the marking tube. Excitation condition in FIG. 5 is the same as that in FIG. 4, the receiving coil 8 enhances the amplitude of the test signal by serially connecting the double-layered coil, which indicates that by using serial connection of multi-layered coils to excite the ultrasonic guided wave at a high frequency, it is possible to ensure the amplitude of the test signal, and to improve test accuracy. It can be seen from test results that the test method and the test device of the invention feature good test effect, convenient installation of sensors, and a high test efficiency, and can meet requirement for on-site test.

While preferred embodiments of the invention have been described above, the invention is not limited to disclosure in these embodiments and the accompanying drawings. Any changes or modifications without departing from the spirit of the invention fall within the scope of the invention.

What is claimed is:

1. A test sensor using a magnetostrictively induced guided wave based on an open magnetic circuit, comprising an excitation coil, a receiving coil and a magnetic device, wherein said magnetic device comprises multiple test modules circumferentially and uniformly disposed thereon so as to be secured to the outer side of a to-be-tested slender component;

each test module comprises a housing, a permanent magnet and a magnetic plate, said permanent magnet is fixedly disposed in said housing, a polarization direction thereof is vertical to an axis of said to-be-tested slender component, and said magnetic plate is fixedly disposed on said housing and in contact with said to-be-tested slender component;

an end of each permanent magnet in the vicinity of said slender component is of the same polarity;

two adjacent housings are connected to each other via an adjusting device, said adjusting device comprises an adjusting slider and a pair of adjusting screws, a strip-shaped hole is disposed on said adjusting slider, and said adjusting screws pass through said adjusting slider via said strip-shaped hole, and are fixedly connected to said housing;

said excitation coil and said receiving coil are coaxially fit on the outer side of said to-be-tested slender component, said excitation coil operates to generate an alternating magnetic field along an axis of said to-be-tested slender component on the surface thereof after sinusoidal alternating current is input, said alternating magnetic field interacts with a static magnetic field generated by said permanent magnet along an axis of said slender component, and further excites a longitudinal ultrasonic guided wave to generate induced voltage in said receiving coil, and a computer determines whether a defect occurs in said to-be-tested slender component after receiving said induced voltage.

2. The test sensor using a magnetostrictively induced guided wave based on an open magnetic circuit of claim 1, wherein said housing comprises a body and an end cover, said body and said end cover are made from non-magnetic materials, and said end cover is disposed on said body, and operates to enclose said permanent magnet along with said body.

3. The test sensor using a magnetostrictively induced guided wave based on an open magnetic circuit of claim 1, wherein said magnetic plate is made of industrial pure iron or low carbon steel.

4. The test sensor using a magnetostrictively induced guided wave based on an open magnetic circuit of claim 1, said excitation coil or said receiving coil is made by winding multiple layers of wires.

5. The test sensor using a magnetostrictively induced guided wave based on an open magnetic circuit of claim 1, wherein said excitation coil and said receiving coil are respectively disposed in the vicinity of both sides of said housing.

6. A test device, comprising the test sensor of claim 1, a signal generator, a power amplifier, a signal pre-processor, an A/D converter and the computer, wherein said power amplifier is electrically connected to an excitation coil, said signal pre-processor is electrically connected to a receiving coil, said computer controls said signal generator to generate a sinusoidal pulse current signal, said sinusoidal pulse current signal is input to said excitation coil after being amplified by said power amplifier, and excites a longitudinal ultrasonic guided wave in a to-be-tested slender component, an electric signal generated by said longitudinal ultrasonic guided wave in said receiving coil is processed by said signal pre-processor and said A/D converter, and input to said computer thereby generating an ultrasonic guided wave test signal to detect whether a defect occurs in said to-be-tested slender component.

\* \* \* \* \*